United States Patent [19]

Bell et al.

[11] Patent Number: 4,617,288

[45] Date of Patent: Oct. 14, 1986

[54] LOW NITROGEN IRON-CONTAINING FISCHER-TROPSCH CATALYST FOR CONVERSION OF SYNTHESIS GAS AND PROCESS FOR PREPARING THE CATALYST

[75] Inventors: Weldon K. Bell, Pennington; Werner O. Haag, Lawrenceville; Garry W. Kirker, Sewell; Donald J. Klocke, Somerdale, all of N.J.

[73] Assignee: Mobil Oil Corporation, New York, N.Y.

[21] Appl. No.: 687,695

[22] Filed: Dec. 31, 1984

[51] Int. Cl.$^4$ .................. B01J 23/72; B01J 23/80; B01J 23/85; B01J 23/89
[52] U.S. Cl. ........................... 502/331; 502/313; 502/325; 502/326; 502/329; 502/330; 502/336; 518/713; 518/715
[58] Field of Search .............. 502/313, 325, 326, 329, 502/330, 331, 336; 518/713, 715

[56] References Cited

U.S. PATENT DOCUMENTS 2,753,367  7/1956  Rottig et al. .................. 502/331 X
2,767,202  10/1956  Rottig .............................. 502/331

FOREIGN PATENT DOCUMENTS

76/4203  11/1977  South Africa .

*Primary Examiner*—W. J. Shine
*Attorney, Agent, or Firm*—A. J. McKillop; M. G. Gilman; L. P. Hobbes

[57] ABSTRACT

Synthesis gas (a mixture of hydrogen gas and carbon monoxide) is converted to hydrocarbons by flowing the gas first over iron-containing Fischer-Tropsch catalyst and then over a zeolite. The Fischer-Tropsch catalyst contains relatively little nitrogen as a result of its preparation by continuous precipitation at a pH ranging from about 6.6 to 6.9 and a temperature ranging from about 80° to about 100° C.

16 Claims, 1 Drawing Figure

U.S. Patent
Oct. 14, 1986
4,617,288
CONTINUOUS PREPARATION REACTOR FOR PRECIPITATED IRON CATALYSTS
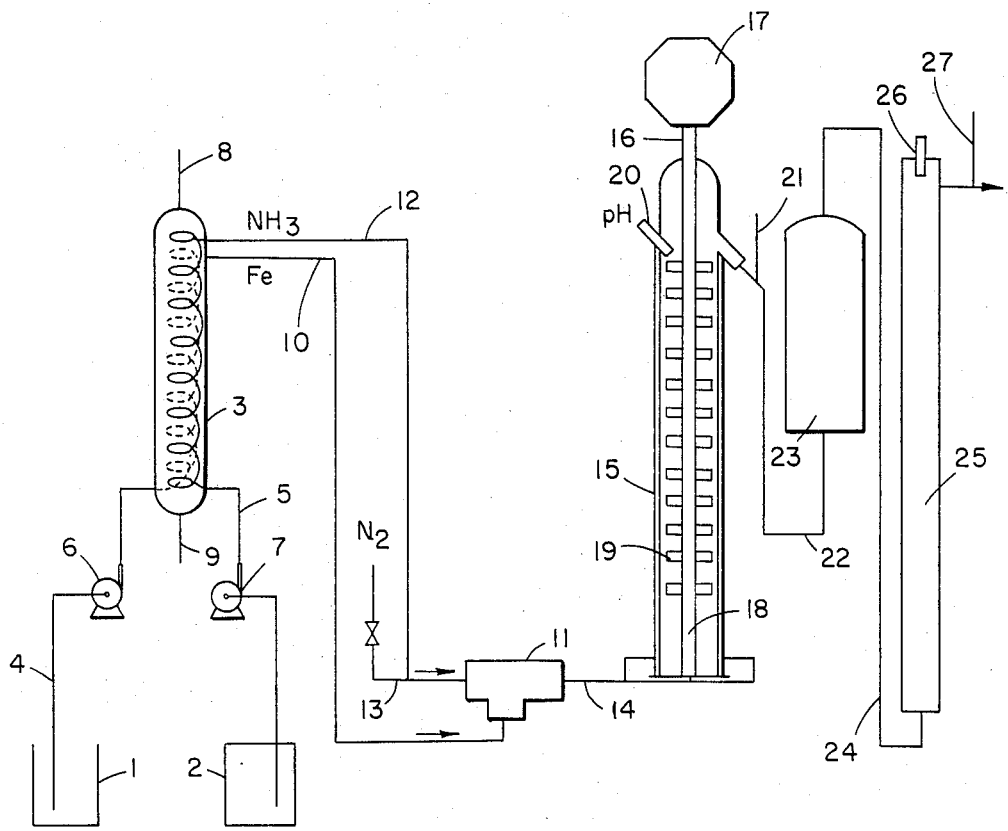

LOW NITROGEN IRON-CONTAINING FISCHER-TROPSCH CATALYST FOR CONVERSION OF SYNTHESIS GAS AND PROCESS FOR PREPARING THE CATALYST

This invention is concerned with low nitrogen Fischer-Tropsch catalyst, a method of preparing such catalyst, and an improved process for converting synthesis gas, i.e. mixtures of gaseous carbon oxides with hydrogen or hydrogen donors, to hydrocarbon mixtures.

Processes are known for converting coal and other hydrocarbons, such as natural gas, to a gaseous mixture consisting essentially of hydrogen and carbon monoxide and/or dioxide. Those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels is given in Encyclopedia of Chemical Technology, Edited by Kirk-Othmer, Third Editon, Vblume 11, pages 410-446 (1980), John Wiley and Sons, New York, N.Y.

It is also known that synthesis gas will undergo conversion to reduction products of carbon monoxide, such as hydrocarbons, at from about 149° C. to about 454° C. (about 300° F. to about 850° F.), under from about one to one thousand atmospheres pressure, over a fairly wide variety of catalysts. The Fischer-Tropsch (F-T) process, for example, which has been most extensively studied, produces a range of liquid hydrocarbons, a portion of which have been used as low octane gasoline. Catalysts that have been studied for this and related processes include those based on iron, cobalt, nickel, ruthenium, thorium, rhodium and osmium, or their oxides.

Recently, it has been discovered that the conversion of synthesis gas into valuable products can be greatly enhanced by employing a special type of crystalline zeolite exemplified by ZSM-5 in admixture with a carbon monoxide reduction catalyst. Thus, for example, in U.S. Pat. No. 4,086,262, incorporated herein by reference, there is disclosed a process for the conversion of syngas by passing the same at elevated temperature over a catalyst which comprises an intimate mixture of a Fischer-Tropsch component and a shape-selective zeolite such as ZSM-5. Said patent points out that the products produced are hydrocarbon mixtures which are useful in the manufacture of heating oil, high octane gasoline, aromatic compounds, and chemical intermediates.

More recently it has been discovered that a highly aromatic or highly olefinic gasoline of enhanced octane number or a gasoline plus distillate mixture can be obtained in greater yield from synthesis gas utilizing a selected synthesis gas composition of low $H_2/CO$ ratio in a specialized Fischer-Tropsch syngas conversion operation and in a sequentially arranged dual reactor conversion process. Such a process is described in U.S. Pat. No. 4,279,830, which is incorporated herein by reference. The process basically is a two-stage process comprising reacting the syngas mixture in a first stage in the presence of a special Fischer-Tropsch CO reducing catalyst under preselected conditions. The product obtained from this first stage syngas conversion is thereafter processed in a second stage reactor with a shape-selective crystalline zeolite catalyst of a desired activity to yield a synthetic hydrocarbon product containing a gasoline fraction boiling less than 204° C. (400° F.).

U.S. application Ser. No. 384,693 filed June 3, 1982, incorporated herein by reference, teaches a two-stage syngas conversion process utilizing a first-stage, iron-containing F-T catalyst whose nitrogen content is reduced by a hydrogen pretreatment. The low nitrogen content of the F-T catalyst results in a reduction in nitrogen contamination of the second stage catalyst.

U.S. application Ser. No. 573,767 filed Jan. 25, 1984, now abandoned, incorporated herein by reference, teaches the preparation of Fischer-Tropsch catalyst wherein nitrogen content is minimized by a high temperature calcination step (371° to 649° C.). The precipitation pH is maintained at anywhere from about 6 to 8. No indication is given that the precipitation is critical to the nitrogen content.

South African Patent Application No. 76/4203 describes a method of preparing Fischer-Tropsch iron-containing catalysts wherein the final precipitation pH is maintained at between 6.6 and 6.9. Control of the pH is believed to determine the pore size distribution of the precipitated catalyst. Precipitation temperature may range from the freezing point to the boiling point and is not considered critical to the pore size distribution of the reaction mixture.

The present invention is concerned primarily with the catalysts employed in the first reactor or first-stage of the above-described two-stage process. These catalysts ordinarily include Fischer-Tropsch synthesis catalysts which contain (1) hydrocarbon synthesis activity, and (2) activity for water-gas shift reactions. Some Fischer-Tropsch catalysts possess activity for accomplishing both of these basic reactions, for example, iron-containing Fischer-Tropsch catalyst. Other catalysts, such as those containing cobalt or ruthenium, function essentially to catalyze only the synthesis reaction. Preferred catalysts for this first phase of the Fischer-Tropsch process include iron with or without copper. Such catalysts may also be promoted with an alkali metal such as potassium.

Ordinarily the iron copper catalyst is prepared by precipitating the iron from an aqueous solution of a nitrate salt. The iron catalyst after precipitation is subsequently calcined at a temperature of about 300° C. Although calcination removes most of the nitrogen present in the catalyst, the catalyst may still contain up to 5000 ppm residual nitrogen. When such a catalyst is used in the previously described two-stage process employing a downstream second-stage zeolite bed, residual nitrogen present in the upstream, first-stage catalyst bed is slowly removed by the stream of synthesis gas and is deposited on the second-stage zeolite catalyst. The deposited nitrogen eventually deactivates the second stage zeolite catalyst so that its effectiveness in converting the effluent gas from the first-stage to aromatic hydrocarbons is seriously diminished. Iron catalysts prepared from iron and copper compounds having organic anions such as oxalates, essentially free of residual nitrogen, often do not enjoy sufficient stability for the conversion of hydrocarbons. These catalysts age more rapidly than those prepared from nitrate salts. Water washing to remove residual nitrogen from the nitrate prepared catalyst is tedious and not entirely effective. Although attempts to remove the nitrogen by higher calcination temperatures, 454°-510° C. (850°-950° F.), as taught in U.S. patent application Ser. No. 573,767, filed Jan. 25, 1984, now abandoned, result in lower residual nitrogen concentration, the stability of the catalyst may be deleteriously affected.

It has now been discovered that two stage processes wherein synthesis gas is first flowed through a bed of precipitated iron catalyst and the effluent therefrom is then passed into a zeolite bed, perform more efficiently if the precipitated iron catalyst employed in the first stage is prepared by a specific process. This process comprises precipitating an aqueous solution containing iron nitrate with aqueous ammonia at a pH ranging greater than about 6.3 and a temperature ranging from about 80° to 100° C. The resulting Fischer-Tropsch catalyst enjoys reduced nitrogen content which prevents subsequent poisoning of the downstream zeolite catalyst. In one aspect, the present invention relates to a process for converting syngas to hydrocarbons which comprises: (a) contacting an iron-containing Fischer-Tropsch catalyst with a syngas stream under conditions effective to achieve high conversion of the syngas to substantial amounts of $C_3+$ carbon compounds; (b) contacting the effluent stream from (a) with a shape-selective crystalline zeolite having a constraint index of about 1 to 12; and (c) recovering from the effluent stream of (b) gasoline and distillate materials. More particularly, the present invention comprises utilizing in the foregoing process an iron-containing Fischer-Tropsch catalyst prepared by a process which comprises precipitating an aqueous solution containing iron nitrate with excess amounts of aqueous ammonia at a pH greater than about 6.3, for example, ranging from about 6.5 to 6.9, preferably 6.6 to 6.8, and a temperature ranging from about 80° to 100° C. The resulting Fischer-Tropsch catalyst contains less than about 1000 ppm nitrogen. The nitrogen level of the preferred Fischer-Tropsch catalyst may be less than about 500, 300, 200 or even 100 ppm nitrogen. The present invention is particularly useful in large scale preparation of Fischer-Tropsch catalysts, such as continuous precipitatior, wherein the nitrogen content of the product is difficult to control.

The Fischer-Tropsch catalyst employed in the present invention may contain up to about 30 weight percent of an additional promoter metal or compounds thereof, such as those selected from the group consisting of copper, manganese, aluminum, silicon, molybdenum, zirconium, palladium, chromium and zinc.

The synthesis gas converted in the combination process of the invention may be prepared from fossil fuels by any one of the known methods, including in-situ gasification processes by the underground partial combustion of coal and petroleum deposits. The term fossil fuels, as used herein, is intended to include anthracite and bituminous coal, lignite, crude petroleum, shale oil, oil from tar sands, natural gas as well as fuels derived from simple physical separations or more profound transformations of these materials, including coked coal, petroleum coke, gas oil, residue from petroleum distillation, coke oven gas rich in CO, or any two or more of the foregoing materials in combination. Other carbonaceous fuels such as peat, wood and cellulosic waste materials also may be used.

The raw synthesis gas produced from fossil fuels will contain various materials and impurities such as particulates, sulfur, methane and metal carbonyl compounds, and will be characterized by a hydrogen-to-carbon oxides ratio which will depend on the fossil fuel and the particular gasification technology utilized. In general, it is desirable for improving the efficiency of subsequent conversion steps to purify the raw synthesis gas by the removal of impurities and provide a relatively clean mixture of hydrogen and carbon oxides. Techniques for such purification are known and are not part of this invention. Should the purified synthesis gas be excessively rich in carbon monoxide, it may be brought within the preferred range by the well known water-gas shift reaction. It is also contemplated that water may be charged with low $H_2/CO$ ratio gas passed to the Fisher-Tropsch operation. The syngas mixtures employed are preferably obtained by low cost syngas generation means.

The synthesis gas used in this invention includes art-recognized equivalents to the already-described mixtures of hydrogen gas with gaseous carbon oxides. Mixtures of carbon monoxide and steam, for example, or of carbon dioxide and hydrogen, to provide synthesis gas by in-situ reaction are suitable.

The catalyts employed in the first stage reactor of this invention contain precipitated iron and exhibit (1) hydrocarbon synthesis activity and (2) activity for water-gas shift reaction. The two basic reactions accomplished with such catalysts are shown below in idealized form:

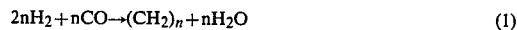
$$2nH_2 + nCO \rightarrow (CH_2)_n + nH_2O \qquad (1)$$

$$H_2O + CO \rightleftharpoons CO_2 + H_2 \qquad (2)$$

where $(CH_2)n$ stands for the hydrocarbons produced. The synthesis catalysts used in the first reactor may contain additional promoters such as alkali metals, alkaline earth metals (Group II), zinc oxide, vanadia, zirconia, copper. etc. Preferred catalysts include potassium promoted iron (Fe(K)) with and without copper. Sources of promoter metal include copper (II) acetate, copper (II) choride and copper (II) nitrate which is particularly preferred.

The shape-selective crystalline zeolites utilized in the second-stage process of this invention are members of a novel class of zeolitic materials which exhibit unusual properties. Preferably said zeolites have been steamed to an alpha value of between 10 and 100. The term "alpha" is well known to those in the art and is described and defined, for example, in U.S. Pat. No. 4,090,981 which is incorporated herein by reference. Techniques of steam treating are also well known to those skilled in the art. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type.

Zeolites utilized in the second stage reactor of the present invention may have a silica to alumina ratio ranging from about 12 to infinity. Highly siliceous zeolites of the present invention have a silica to alumina ratio ranging from about 40 to greater than 200. Zeolites of generally lower silica to alumina ratios, say, less than about 70, are made from solutions containing soluble aluminum compounds such as alum. Zeolites of higher silica to alumina ratio (e.g., greater than about 70) of the present invention can be made from caustic forming solutions containing NaOH, water, amorphous precipitated silica, and no intentionally added aluminum.

The siliceous zeolite crystals produced by the method of the present invention also exhibit constrained access to and egress from their intercrystalline free space inasmuch as they have a constraint index of from 1 to 12. Such zeolite materials which have a silica to alumina molar ratio of at least 12 and a constraint index within the range of 1 to 12 are well known. Such zeolites and their use as catalysts for the conversion of organic compounds are generally described, for example, in U.S. Pat. No. 4,326,994. Crystalline zeolites of the preferred type prepared in accordance with the method of the present invention include those having the structure of zeolite beta, ZSM-5, ZSM-5/ZSM-11 intermediate, ZSM-11, ZSM-12, ZSM-23, ZSM-35, ZSM-38, and ZSM-48, with ZSM-5 being particularly preferred.

Zeolite beta is described in greater detail in U.S. Pat. Nos. 3,308,069 and Re. 28,341, which patents disclose in particular the X-ray diffraction pattern of and a synthesis method for zeolite beta.

ZSM-5 is described in greater detail in U.S. Pat. Nos. 3,702,883 and Re. 29,948, which patents provide the X-ray diffraction pattern of and a synthesis method for the therein disclosed ZSM-5.

ZSM-11 is described in U.S. Pat. No. 3,709,979, which discloses in particular the X-ray diffraction pattern of and a synthesis method for ZSM-11.

ZSM-5/ZSM-11 intermediate is desoribed in U.S. Pat. No. 4,229,424, which discloses in particular the X-ray diffraction pattern of and a synthesis method for ZSM-5/ZSM-11 intermediate.

ZSM-12 is described in U.S. Pat. No. 3,832,449, which discloses in particular the X-Ray diffraction pattern of and a synthesis method for ZSM-12.

ZSM-23 is described in U.S. Pat. No. 4,076,842, which discloses in particular the X-ray diffraction pattern of and a synthesis method for ZSM-23.

ZSM-35 is described in U.S. Pat. No. 4,016,245, which discloses in particular the X-ray diffraction pattern of and a synthesis method for ZSM-35.

ZSM-38 is described in U.S. Pat. No. 4,046,859, which discloses in particular the X-ray diffraction pattern of and a synthesis method for ZSM-38.

ZSM-48 is described in U.S. Pat. No. 4,375,573, which discloses in particular the X-ray diffraction pattern of and a synthesis method for ZSM-48.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

In carrying out the process of the present invention, the synthesis gas to be processed can be introduced and flowed through the first stage reactor in contact with the catalyst. Preferably the catalyst to be used will be an iron-copper catalyst promoted with potassium carbonate. The effluent from the first-stage reactor is then passed directly to the second stage or zeolite catalyst conversion reactor. Operating conditions in the first stage can be conducted at a temperature of between about 232° C. to 288° C. (450° F. to 550° F.) and a pressure of about 446 to about 2170 kPa (50 to 700 psig) and a gas flow rate of about 0.3 to 7 normal liters per gram of catalyst per hour, a normal liter of gas being the volume of gas measured at 16° C. (60° F.) at 101.3 kPa (0 psig). Operating conditions in the second-stage reactor can be about 260° to 482° C. (500° F. to 900° F.), about 446 to about 2170 kPa (50 to 700 psig) and a weight hourly space velocity of about 0.3 to 5 (preferably about 0.5 to 2) weight of hydrocarbon per weight of catalyst per hour. The effluent from this second-stage reactor is then processed to separate therefrom the desired gasoline and distillate fractions.

The first-stage Fischer-Tropsch catalyst utilized in the present invention can be prepared by continuously precipitating an aqueous iron nitrate solution with greater than stoichiometric amounts of ammonia or ammonium cation. Ammonia may be added in any suitable form, for example as gaseous or liquid ammonia, or aqueous ammonium hydroxide solutions of about 1 to 20 wt %, preferably about 2 to 5 wt % ammonium hydroxide. In addition, any suitable ammonium salt such as ammonium carbonate may be used in lieu of ammonia.

The solution may contain anywhere from about 0.1 to about 2 moles per liter of ferric ion. Preferably about 0.5 to about 1 mole per liter is used in order to avoid low production rates encountered at dilute concentrations and the formation of unmanageable slurries at high concentrations. In order to obtain the desired low-nitrogen Fischer-Tropsch catalyst, conditions during precipitation are maintained above a pH of about 6.3, say at a pH of about 6.5 to 6.9 and a temperature of about 70° to 100° C., preferably about 80° to 90° C. pH ranges of about 6.6 to 6.8 are particularly preferred when precipitation is carried out in a continuous precipitation reactor.

Control of pH is maintained during the precipitation process by any suitable method, including the addition of acidic or basic reagents, to the reaction mixture, In a particularly preferred embodiment, ammonia or ammonium ion is added in such amounts as to effect the desired pH.

The iron nitrate aqueous solution precipitated by the addition of ammonia may also contain other promoting metals such as copper, manganese, aluminum, molybdenum, palladium, chromium and zinc at levels below about 30 weight percent of Fe content, preferably about 0.1 to 10 weight percent. Upon the addition of excess amounts of ammonia or ammonium ion to the iron nitrate-containing aqueous solution to form a precipitate-containing product, a gel is formed. Maintaining a temperature of about 70° to 100° C. desirably results in the gel rapidly attaining precipitation pH. The gel is matured at precipitation conditions for anywhere from about 0.1 to 50 hours, preferably about 1 to 15 minutes. The resulting precipitate-containing mixture may be refluxed for anywhere from about 0.25 to 50 hours, preferably about 0.25 to 10 hours. The reflux product may then be washed with an initial aqueous wash solution, for example, water, which is preferably maintained at a temperature of about 80° to 95° C. Up to 20 liters of the wash solution may be added for each mole of iron in the precipitate-containing mixture. The washed product may then be filtered immediately. Additional promoting materials may be added to the final wash mixture prior to the filtering step or the filtered product may be contacted with a solution which contains a source of additional promoter. For example, alkali metal such as potassium may be added to the precipitated iron catalyst by slurrying and contacting the filtered product containing about 0.1 to 6 g of potassium carbonate per 100 g of iron with sufficient water to form a final slurry containing about 0.0006 to 0.34 weight percent potassium and 1 to 10 weight percent iron, preferably about 3 to 4 weight percent iron. The resulting slurry may then be filtered. The filtered product, with or without additional promoter metal may then be dried under suitable conditions such as temperatures ranging from about 50° to 120° C., preferably about 100° to 120° C. for a period of about 10 to 72 hours, preferably about 18 to 24 hours.

Particularly desirable sources of promoter metal include salts or hydroxides of potassium, cesium, sodium and rubidium. Such metals may also be added in the form of bicarbonates or carbonates of the desired promoter metal. It is generally preferred that nitrate, chloride and sulfate salts of said promoter metal not be used as sources of promoter metals because these anions can lead to a less active catalyst.

After drying, the product may be crushed to a desired particle size of less than about 2.6 mm and is thereafter calcined, preferably in an oxygen-containing medium such as air, at a temperature of 200° to 400° C. for about 0.1 to 100 hours, preferably about 300° to 350° C. for about 2 to 10 hours.

The resulting catalyst will contain very small amounts of nitrogen and is therefore particularly suited for Fischer-Tropsch conversions of synthesis gas which utilize a subsequent hydrocarbon conversion with shape-selective zeolite material susceptible to poisoning by the basic nitrogen compounds which are often formed by nitrogen-containing Fischer-Tropsch catalysts.

The following examples disclosed below are merely exemplary and are not to be construed as limiting the scope of the present invention.

BRIEF DESCRIPTION OF THE DRAWING

The FIGURE depicts a continuous preparation reactor for precipitated iron catalysts.

EXAMPLE 1—Continuous Preparation of Potassium Promoted Fe/Cu Fischer-Tropsch Catalyst at a pH of 6.8±0.1

A copper-containing ferric nitrate solution was prepared by adding 16.5 kg $Fe(NO_3)_3.9H_2O$ to 42 l of deionized water. A solution of 20 g $Cu(NO_3)_2.2.5H_2O$ in 200 ml of deionized water was then added. The resulting solution was heated to about 80° C. and placed in vessel (1) of the FIGURE. An aqueous ammonia solution was prepared by adding 10.1 kg of concentrated aqueous ammonia solution containing about 29.6 weight percent ammonia to 110 kg deionized water. The resulting solution maintained at room temperature was added to vessel (2). The iron solution was pumped from vessel (1) to solution preheater (3) through conduit (4) by means of pump (6) at a rate of about 200 to 300 cc/minute. Aqueous ammonia was pumped from vessel (2) to solution preheater (3) via conduit (5) by means of pump (7) at a rate of about 500–600 cc/minute The solution flows were heated without intermixing in the solution preheater employing steam as the heating medium. Steam was passed into the preheater via steam inlet (8) and exited through steam outlet (9). The preheated iron solution passed from the preheater through conduit (10) to mixing nozzle (11) wherein it was combined with ammonia passed from the preheater to the mixing nozzle via conduit (12). Nitrogen was introduced to the mixing nozzle via conduits (13) and (12). The resulting mixture emerged from the mixing nozzle and passed through conduit (14) into a steam-jacketed continuous precipitation apparatus (15) containing a motorized mixing means (16) comprising a motor (17) connected to a shaft (18) on which were mounted mixing blades (19). At the upper portion of the apparatus, a pH-sensing means (20) and a heat sensing means (21) monitored the reactor effluent. The temperature at (21) ranged from about 70° to 80° C. The effluent passed from the reactor through conduit (22) to a steam-jacketed heat exchanger (23) and thence through a conduit (24) to a stationary mixer (25) at whose downstream end was pH-sensing means (26) and heat sensing means (27). The temperature at (27) was maintained at about 93° to 100° C., while the pH at (26) was maintained at about 6.8±0.1. The stationary mixer effluent was vacuum filtered and washed with about 200 l of deionized water until free of nitrates, as shown by the diphenylamine test. The filter cake was reduced to a wet cake of 15 weight percent water which was slurried with about 580 ml of an aqueous solution containing about 8 g/l of $K_2CO_3$. The slurry was dried at about 110° C., crushed to less than #8 mesh size and calcined at 300° C. with 10 cc air/g catalyst per minute. Catalyst destined for use in a slurry reactor was further treated by ball milling in oil for about 12 hours.

Example 2 - Continuous Preparation of Potassium Promoted Fe/Cu Fischer-Tropsch Catalyst at a pH of about 6.0

The precipitation procedure of Example 1 was followed except that the pH at (26) was maintained at about 6.0. A comparison of the properties of the catalysts of Examples 1 and 2 is set out in Table 1 and indicates the effect of precipitation pH on nitrogen levels.

TABLE 1

Effect of Precipitation pH on N—Levels of F-T Catalysts Prepared by Continuous Precipitation

| Example | Wt Ratio Fe/Cu/$K_2CO_3$ | pH[1] | Nitrogen (ppm)[2] |
|---|---|---|---|
| 2 | 100/3/0.6 | 6.0 | 5600 |
| 1 | 100/0.2/0.25 | 6.8 | 49 |

1 - pH measured at the highest temperature of the precipitate slurry (90–97° C.).
2 - Nitrogen content of calcined catalyst (calcined @ 300° C. for 6 hours in air).
3 - Fe present largely as $Fe_2O_3$ in fresh catalyst.

It is claimed:

1. In a process for preparing an iron-containing Fischer-Tropsch catalyst by continuously precipitating an aqueous solution containing iron nitrate with aqueous amonia, to form a precipitate-containing product which is thereafter dried, the improvement whereby a catalyst containing less than 500 ppm nitrogen is produced which comprises maintaining a pH of about 6.5 to 6.9 and a temperature of about 70° to 100° C. during precipitation.

2. The process of claim 1 wherein said catalyst contains less than about 300 ppm nitrogen, said pH is about 6.8 and said temperature is about 80° to 90° C.

3. The process of claim 1 wherein said catalyst contains less than about 200 ppm nitrogen.

4. The process of claim 1 wherein said catalyst contains less than about 100 ppm nitrogen.

5. The process of claim 2 wherein the aqueous solution containing iron nitrate contains less than about 30 g of a source of additional promoter metal, selected from the group consisting of Co, Mo, Al, Pd, Cr, Zn and Cu, per 100 g of iron.

6. The process of claim 1 wherein said precipitate-containing product is refluxed, washed with an initial aqueous wash solution, filtered to recover said precipitate which is thereafter washed with a second aqueous wash solution and dried.

7. The process of claim 6 wherein at least one of said aqueous wash solutions contains a source of promoter metal selected from the group consisting of Co, Mo, Al, Pd, Cr, Zn and alkali metal.

8. The process of claim 7 wherein said source of promoter metal comprises a salt of an alkali metal.

9. The process of claim 8 wherein said salt contains a carbonate anion.

10. The process of claim 8 wherein said salt contains a bicarbonate anion.

11. The process of claim 7 wherein said source of promoter metal comprises an alkali metal hydroxide.

12. The process of claim 8 wherein said alkali metal is potassium.

13. The process of claim 11 wherein said alkali metal is potassium.

14. The process of claim 5 wherein said source of additional promoter metal is copper (II) nitrate.

15. The process of claim 6 wherein the dried product is crushed to a particle size of less than about 2.6 mm.

16. An iron-containing Fischer-Tropsch catalyst containing less than about 300 ppm nitrogen prepared by a process which comprises continuously precipitating a forming mixture containing an aqueous ferric nitrate solution and excess amounts of aqueous ammonia wherein said forming mixture is maintained at a pH of about, 6.5 to 6.9 and a temperature of about 80° to 90° C. during said precipitation and drying said precipitate.

* * * * *